United States Patent

Annen et al.

[11] Patent Number: 4,777,165
[45] Date of Patent: Oct. 11, 1988

[54] 6α,16β-DIMETHYL CORTICOIDS AND THEIR ANTI-INFLAMMATORY USE

[75] Inventors: Klaus Annen, Münster-Albachten; Henry Laurent, Berlin; Helmut Hofmeister, Berlin; Rudolf Wiechert, Berlin; Michael Topert, Berlin, all of Fed. Rep. of Germany

[73] Assignee: Schering Aktiengesellschaft, Berlin, Fed. Rep. of Germany

[21] Appl. No.: 64,029

[22] Filed: Jun. 17, 1987

Related U.S. Application Data

[63] Continuation of Ser. No. 691,811, Jan. 16, 1985, abandoned.

[30] Foreign Application Priority Data

Jan. 17, 1984 [DE] Fed. Rep. of Germany ....... 3401680

[51] Int. Cl.$^4$ .................. A61K 31/56; C07J 1/00
[52] U.S. Cl. .................. 514/179; 260/397.45
[58] Field of Search .................. 260/397.45; 514/172, 514/179, 180; 540/87, 88, 89

[56] References Cited

U.S. PATENT DOCUMENTS

| | | | |
|---|---|---|---|
| 3,054,811 | 9/1962 | Arth et al. | 260/397.45 |
| 3,152,154 | 10/1964 | Ercoli et al. | 260/397.47 |
| 3,290,388 | 12/1966 | Shapiro et al. | 260/397.4 |
| 4,555,507 | 11/1985 | Annen et al. | 260/397.45 |

FOREIGN PATENT DOCUMENTS 0100874 7/1983 European Pat. Off.
0898292 6/1962 United Kingdom .

Primary Examiner—Leonard Schenkman
Assistant Examiner—Joseph A. Lipovsky
Attorney, Agent, or Firm—Millen & White

[57] ABSTRACT

6α,16β-Dimethyl corticoids of general Formula I

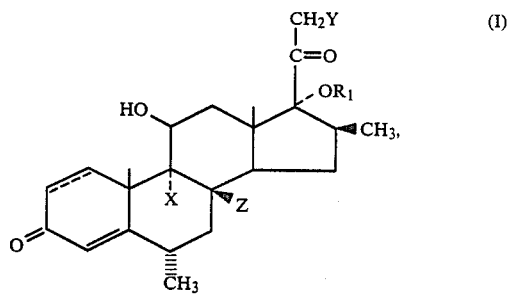

wherein
the bond ------ is a single bond or a double bond, and
X is a hydrogen atom, a fluorine atom, a chlorine atom, or a bromine atom,
Z is a hydrogen atom or, jointly with X, is a carbon-carbon bond,
$R_1$ is a formyl group, an alkanoyl group or alkoxyalkyl group of 2-8 carbon atoms, or a benzoyl group, and
Y is a hydrogen atom or a methyl group,
are pharmacologically active compounds.

7 Claims, No Drawings

6α, 16β-DIMETHYL CORTICOIDS AND THEIR ANTI-INFLAMMATORY USE

This is a continuation of application Ser. No. 691,811 filed Jan. 16, 1985, now abandoned.

BACKGROUND OF THE INVENTION

This invention relates to 6,16-dimethyl corticoids, pharmaceutical preparations containing them, processes for their production and to steroids useful as intermediates for the synthesis of these 6,16-dimethyl corticoids.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing 6α,16β-dimethyl corticoids of Formula I

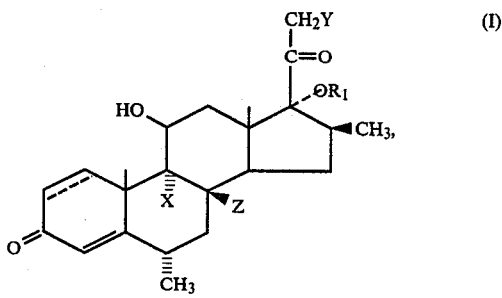

wherein
the bond ------ represents a single bond or a double bond and
X is a hydrogen atom, a fluorine atom, a chlorine atom, or a bromine atom,
Z is a hydrogen atom or, jointly with X, is a carbon-carbon bond,
$R_1$ is a formyl group, an alkanoyl group or alkoxyalkyl group of 2–8 carbon atoms, or a benzoyl group, and
Y is a hydrogen atom or a methyl group.

DETAILED DISCUSSION

The novel 6,16-dimethyl corticoids can contain, as the substituent $R_1$, a formyl group, an alkanoyl group or alkoxyalkyl group of 2–8 (preferably 2–6) carbon atoms, or a benzoyl group. Suitable alkanoyl groups $R_1$ are straight-chained or branched, for example, acetyl, propionyl, butyryl, isobutyryl, valeryl, 3-methylbutyryl, trimethylacetyl, a hexanoyl group, etc. Especially worth mentioning as examples for straight-chained or branched alkoxyalkyl groups are alkoxymethyl groups, e.g., methoxymethyl, ethoxymethyl, propoxymethyl, isopropoxymethyl, butoxymethyl, isobutoxymethyl, tert-butoxymethyl, etc., all other combinations also being possible.

The 6,16-dimethyl corticoids of Formula I are distinguished by a pronounced anti-inflammatory activity when applied topically, e.g., to mammals, including humans. Moreover, they show an excellent dissociation between desirable topical efficacy and undesirable systemic side effects, e.g., systemic anti-inflammatory activity.

It is to be noted that the 6,16-dimethyl corticoids of Formula I wherein X is hydrogen, fluorine, or chlorine are more suited for use in pharmaceutical preparations than those wherein the substituent X is bromine, since the latter preparations are less stable in galenicals. However, all of the Formula I compounds are useful antiinflammatorily. However, on the other hand, the 9-bromo steroids of Formula I are valuable intermediates for the synthesis of the other pharmacologically efficacious 6,16-dimethyl corticoids of this invention.

The novel 6,16-dimethyl corticoids of Formula I are suited, in combination with the excipients customary in galenic pharmacy, for the local treatment of contact dermatitis, eczemas of a great variety of types, neurodermatoses, erythrodermia, burns, pruritis vulvae et ani, rosacea, erythematodes cutaneus, psoriasis, lichen ruber planue et verucosus, and similar skin disorders.

The drug specialties can be prepared in the usual way by converting the active agents together with suitable additives into the desired form of application, such as, for example: solutions, lotions, ointments, creams, or plasters. In the thus-formulated medical agents, the concentration of active ingredient is dependent on the form of application as is conventional. An active agent concentration of 0.001% to 1% is preferably used in lotions and ointments. They are administered analogously to difluocortolone valerianate.

The novel compounds are moreover readily suitable, optionally in combination with the usual excipients and auxiliary agents, also for the preparation of inhalants that can be employed for therapy of allergic diseases of the respiratory tract, for example bronchial asthma or rhinitis. In this application, they are formulated in concentrations of about 0.001 to 1 wt % and administered analogously to beclomethasone dipropionate.

The novel corticoids are furthermore also suitable, in the form of capsules, tablets, or dragees containing preferably 5–200 mg of active ingredient and being administered orally, or in the form of suspensions containing preferably 50–500 mg of active ingredient per dosage unit and being administered rectally, for the treatment of allergic diseases of the intestinal tract, such as colitis ulcerosa and colitis granulomatosa. In these applications they are administered in these dosages typically 1–4 times a day analogously to prednisolone.

The novel 6,16-dimethyl corticoids of Formula I can be produced conventionally according to a process comprising
(a) opening the epoxy ring of a steroid of general Formula II

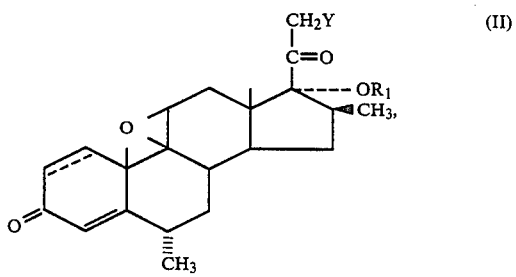

wherein ------, $R_1$ and Y have the meanings given above, with hydrogen fluoride or hydrogen chloride; or (b) chemically adding hypochlorous or hypobromous acid to the $\Delta^{9(11)}$-double bond of a steroid of general Formula III

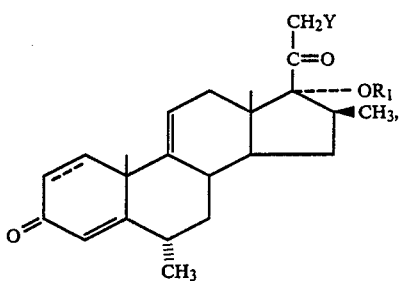

wherein -----, $R_1$ and Y have the meanings given above, and, if desired, eliminating, by reduction, the 9-positioned halogen atom from the 9-bromo steroids of Formula I. or eliminating hydrogen halide for the introduction of the $\Delta^8$-double bond; or dehydrogenating in the 1,2-position a steroid of Formula III saturated in the 1,2-position.

These processes can be conducted under the conditions described in German Patent Application Nos. P 26 45 105 and 26 45 104, as well as in European Application No. 34115 and the equivalent BP Nos. 1594852, 1594371 and U.S. Pat. No. 4,322,349.

Especially noteworthy are the following intermediates of Formula IV

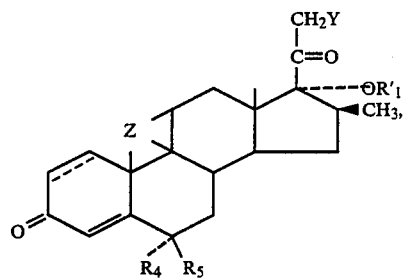

wherein ----- and Y have the meanings given above
$R'_1$ is a hydrogen atom or $R_1$ as defined above
Z is a carbon-carbon bond or an oxygen atom,
$R_4$ and $R_5$ jointly mean a methylene group or
$R_4$ is a hydrogen atom or a methyl group and
$R_5$ is a hydrogen atom.

They can be prepared from the corresponding compounds unsubstituted in the 6-position according to the process of U.S. Pat. No. 4,322,349. Also, one can, for example, transform the 6-position unsubstituted compounds in an inert solvent with formaldehyde dimethylacetal in the presence of phosphoroxychloride at 0°–80° C. to obtain the 6-methylene compounds of Formula IV. These can then be hydrolyzed to the 6-methyl steroids which can be epimerized by means of acids to the 6α-methyl steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are fet forth uncorrected in degrees Celsius; unless otherwise indicated, all parts and percentages are by weight.

EXAMPLE 1

(A) A suspension of 10.0 g of sodium acetate in 300 ml of chloroform and 300 ml of formaldehyde dimethylacetal is stirred with 19 ml of phosphorus oxychloride for one hour at a bath temperature of 65° C. After adding 10.0 g of 17α-hydroxy-16β-methyl-4,9(11)-pregnadiene-3,20-dione, another 19 ml of phosphorus oxychloride is added dropwise and the reaction solution is stirred for another 6.5 hours at 65° C. The cooled-off solution is treated with such an amount of a saturated soda solution that the aqueous phase is made permanently alkaline. The organic phase is separated, washed neutral and concentrated after drying. The crude product is purified on 700 g of silica gel with a hexane-ethyl acetate gradient (0–50% ethyl acetate), thus isolating 5.9 g of 17α-hydroxy-16β-methyl-6-methylene-4,9(11)-pregnadiene-3,20-dione, mp 157°–158° C.

(B) A solution of 3.3 g of 17α-hydroxy-16β-methyl-6-methylene-4,9(11)-pregnadiene-3,20-dione in 40 ml of glacial acetic acid is cooled to 0° C. and stirred, after adding 15 ml of trifluoroacetic acid anhydride dropwise, for one hour at room temperature. After precipitation into ice water-sodium chloride, the mixture is filtered off and worked up as usual. The crude product is purified on 450 g of silica gel with a hexane-ethyl acetate gradient (0–50% ethyl acetate), thus obtaining 2.3 g of 17α-acetoxy-16β-methyl-6-methylene-4,9(11)-pregnadiene-3,20-dione, mp 197°–198° C.

(C) A suspension of 0.5 g of palladium/active carbon in 30 ml of ethanol and 20 ml of cyclohexene is stirred for one hour at a bath temperature of 80° C. and, after adding 4.1 g of 17α-acetoxy-16β-methyl-6-methylene-4,9(11)-pregnadiene-3,20-dione, is heated under agitation for 17.5 hours. After cooling, the catalyst is suctioned off, the mixture is washed with methylene chloride, and the combined filtrates are stirred with 40 ml of concentrated hydrochloric acid for 0.5 hour at room temperature. The reaction solution is concentrated to one-third its volume, poured on ice water, and worked up as usual. The crude product is purified on 400 g of silica gel with a hexane-ethyl acetate gradient (0–50% ethyl acetate). Yield: 3.6 g of 17α-acetoxy-6α,16β-dimethyl-4,9(11)-pregnadiene-3,20-dione, mp 188°–190° C.

(D) A solution of 0.5 g of 17α-acetoxy-6α,16β-dimethyl-4,9(11)-pregnadiene-3,20-dione in 7.7 ml of dioxane and 0.5 ml of water is combined, after adding 380 mg of N-bromosuccinimide, at 20° C. dropwise with a solution of 0.04 ml of 70% strength perchloric acid in 0.6 ml of water. The mixture is agitated for one hour at an internal temperature of 20° C., cooled down to 15° C., and neutralized dropwise with a solution of 1.6 g of sodium acetate and 1.0 g of sodium sulfite in 9.7 ml of water. In this process, the internal temperature must not rise beyond 23° C. After the addition of 5 ml of methanol, the reaction mixture is stirred for 15 minutes at room temperature and, after adding 20 ml of water, for 3 hours at 0° C. Finally, the precipitate is suctioned off, the residue is washed neutral with water and dried at 70° C. in a vacuum-drying cabinet. The crude product is recrystallized from acetone/hexane, thus isolating 380 mg of 17α-acetoxy-9α-bromo-11β-hydroxy-6α,16β-dimethyl-4-pregnene-3,20-dione, mp 162° C. (decomposition).

(E) 490 mg of 17α-acetoxy-9α-bromo-11β-hydroxy-6α,16β-dimethyl-4-pregnene-3,20-dione is dissolved in 10 ml of anhydrous tetrahydrofuran and, after adding 1.5 ml of tributyltin hydride and 40 mg of azobisisobutyronitrile, refluxed for 2 hours. The mixture is concentrated under vacuum and the residue purified on 100 g of silica gel with a hexane-ethyl acetate gradient (0–50% ethyl acetate). Yield: 195 mg of 17α-acetoxy-11β-hydroxy-6α,16β-dimethyl-4-pregnene-3,20-dione, mp 264°–265° C.

EXAMPLE 2

(A) A suspension of 50 g of 17α-hydroxy-16β-methyl-4,9(11)-pregnadiene-3,20-dione in 625 ml of diethyl glycol dimethyl ether is stirred, after adding 75 g of 4-dimethylaminopyridine, with 75 ml of propionic anhydride for 3 days at a bath temperature of 80° C. After ice water precipitation, the mixture is worked up as usual, and the crude product is purified on 3.5 kg of silica gel with a methylene chloride-acetone gradient (0–12% acetone). Yield: 34.2 g of 16β-methyl-17α-propionyloxy-4,9(11)-pregnadiene-3,20-dione, mp 158°–160° C.

(B) Under the conditions of Example 1(A), 53 g of 16β-methyl-17α-propionyloxy-4,9(11)-pregnadiene-3,20-dione is reacted with formaldehyde dimethylacetal to 33.9 g of 16β-methyl-6-methylene-17α-propionyloxy-4,9(11)-pregnadiene-3,20-dione, worked up, and purified; mp 175°–177° C.

(C) 5.0 g of 16β-methyl-6-methylene-17α-propionyloxy-4,9(11)-pregnadiene-3,20-dione is hydrogenated analogously to Example 1(C) with palladium/activated carbon and cyclohexene, worked up, and purified, Yield: 3.7 g of 6α,16β-dimethyl-17α-propionyloxy-4,9(11)-pregnadiene-3,20-dione, mp 129° C.

(D) As described in Example 1(D), 500 mg of 6α,16β-dimethyl-17α-propionyloxy-4,9(11)-pregnadiene-3,20-dione is reacted with N-bromosuccinimide and perchloric acid, worked up, and purified, thus obtaining 520 mg of 9α-bromo-11β-hydroxy-6α,16β-dimethyl-17α-propionyloxy-4-pregnene-3,20-dione, mp 115° C.

(E) Under the conditions of Example 1(E), 550 mg of 9α-bromo-11β-hydroxy-6α,16β-dimethyl-17α-propionyloxy-4-pregnene-3,20-dione is debrominated with tributyltin hydride, worked up, and purified, yielding 280 mg of 11β-hydroxy-6α,16β-dimethyl-17α-propionyloxy-4-pregnene-3,20-dione, mp 214°–215° C.

EXAMPLE 3

(A) A suspension, cooled to 0° C., of 11.1 g of 17α-hydroxy-16β-methyl-4,9(11)-pregnadiene-3,20-dione in 110 ml of butyric acid is combined dropwise with 60 ml of trifluoroacetic anhydride and stirred for 2 hours at room temperature. After precipitation into ice water-sodium chloride, the mixture is worked up and purified as usual. Yield: 7.8 g of 17α-butyryloxy-16β-methyl-4,9(11)-pregnadiene-3,20-dione, mp 131°–132° C.

(B) As described in Example 1(A), 13.0 g of 17α-butyryloxy-16β-methyl-4,9(11)-pregnadiene-3,20-dione is reacted with formaldehyde dimethylacetal, worked up, and purified. Yield: 7.8 g of 17α-butyryloxy-16β-methyl-6-methylene-4,9(11)-pregnadiene-3,20-dione, mp 133° C.

(C) Analogously to Example 1(C), 9.2 g of 17α-butyryloxy-16β-methyl-6-methylene-4,9(11)-pregnadiene-3,20-dione is hydrogenated with palladium/active carbon and cyclohexene, worked up and purified, thus isolating 6.75 g of 17α-butyryloxy-6α,16β-dimethyl-4,9(11)-pregnadiene-3,20-dione, mp 165°–166° C.

(D) 500 mg of 17α-butyryloxy-6α,16β-dimethyl-4,9(11)-pregnadiene-3,20-dione is reacted analogously to Example 1(D) with N-bromosuccinimide and perchloric acid, worked up and purified, thus isolating 420 mg of 9α-bromo-17α-butyryloxy-11β-hydroxy-6α,16β-dimethyl-4-pregnene-3,20-dione, mp 158°–159° C.

(E) Under the conditions of Example 1(E), 500 mg of 9α-bromo-17α-butyryloxy-11β-hydroxy-6α,16β-dimethyl-4-pregnene-3,20-dione is debrominated with tributyltin hydride, worked up and purified, yielding 284 mg of 17α-butyryloxy-11β-hydroxy-6α,16β-dimethyl-4-pregnene-3,20-dione, mp 98°–100° C.

EXAMPLE 4

(A) A solution of 13.0 g of 17α-hydroxy-16β-methyl-6-methylene-4,9(11)-pregnadiene-3,20-dione in 100 ml of methylene chloride is combined, after adding 26.0 g of benzoic acid, at room temperature dropwise with 120 ml of trifluoroacetic acid anhydride and stirred for 0.5 hour. After the usual working-up process, the crude product is purified on 700 g of silica gel with a hexane-ethyl acetate gradient (0–30% ethyl acetate), thus isolating 3.2 g of 17α-benzoyloxy-16β-methyl-6-methylene-4,9(11)-pregnadiene-3,20-dione.

(B) Under the conditions of Example 1(C), 3.8 g of 17α-benzoyloxy-16β-methyl-6-methylene-4,9(11)-pregnadiene-3,20-dione is hydrogenated with palladium/active carbon and cyclohexene, worked up and purified, yielding 1.6 g of 17α-benzoyloxy-6α,16β-dimethyl-4,9(11)-pregnadiene-3,20-dione.

(C) Analogously to Example 1(D), 1.5 g of 17α-benzoyloxy-6α,16β-dimethyl-4,9(11)-pregnadiene-3,20-dione is reacted with N-bromosuccinimide and perchloric acid, worked up and purified, thus obtaining 1.1 g of 17α-benzoyloxy-9α-bromo-11β-hydroxy-6α,16β-dimethyl-4-pregnene-3,20-dione.

(D) As described in Example 1(E), 1.0 g of 17α-benzoyloxy-9α-bromo-11β-hydroxy-6α,16β-dimethyl-4-pregnene-3,20-dione is debrominated with tributyltin hydride, worked up, and purified. Yield: 695 mg of 17α-benzoyloxy-11β-hydroxy-6α,16β-dimethyl-4-pregnene-3,20-dione.

EXAMPLE 5

(A) 3.5 g of 17α-hydroxy-6α,16β-dimethyl-4,9(11)-pregnadiene-3,20-dione, prepared analogously to Example 1(C) from 17α-hydroxy-16β-methyl-6-methylene-4,9(11)-pregnadiene-3,20-dione, is dissolved in 25 ml of anhydrous methylene chloride and 16 ml of formaldehyde dimethylacetal and combined in incremental portions with a mixture of 5.0 g of kieselguhr W20 and 2.5 g of phosphorus pentoxide. The mixture is stirred for 45 minutes at room temperature, suctioned off, and the residue eluted repeatedly with methylene chloride containing 3–5% triethylamine. The crude product is purified on 500 g of silica gel with a methylene chloride-acetone gradient (0–10% acetone). Yield: 2.2 g of 17α-methoxymethoxy-6α,16β-dimethyl-4,9(11)-pregnadiene-3,20-dione.

(B) Under the conditions of Example 1(D), 2.0 g of 17α-methoxymethoxy-6α,16β-dimethyl-4,9(11)-pregnadiene-3,20-dione is reacted with N-bromosuccinimide, worked up and purified, yielding 1.7 g of 9α-bromo-11β-hydroxy-17α-methoxymethoxy-6α,16β-dimethyl-4-pregnene-3,20-dione.

(C) Analogously to Example 1(E), 1.2 g of 9α-bromo-11β-hydroxy-17α-methoxymethoxy-6α,16β-dimethyl-4-pregnene-3,20-dione is debrominated with tributyltin hydride, worked up and purified, thus isolating 850 mg of 11β-hydroxy-17α-methoxymethoxy-6α,16β-dimethyl-4-pregnene-3,20-dione.

EXAMPLE 6

(A) A solution of 3.0 g of 17α-acetoxy-6α,16β-dimethyl-4,9(11)-pregnadiene-3,20-dione in 61 ml of dioxane is refluxed for 7 hours with 3.0 g of dichlorodicyanobenzoquinone. After cooling and filtration, the filtrate is concentrated to dryness. The crude product is purified on 750 g of silica gel with a hexane-ethyl acetate gradient (0–50% ethyl acetate). Yield of crude product: 1.3 g of 17α-acetoxy-6α,16β-dimethyl-1,4,9(11)-pregnatriene-3,20-dione; this product is treated in 20 ml of boiling ethanol dropwise with a solution of 5.73 g of $Na_2S_2O_5$ in 8 ml of water. After 2 hours, the reaction mixture is distilled in such a way that the volume in the distillation alembic remains the same by adding water, and the bridge thermometer indicates 99° C. The distillation alembic is cooled to +20° C., the mixture is filtered off, the residue is washed thoroughly with water and dissolved in methylene chloride. The organic solution is filtered after drying over a silica gel layer and subsequently concentrated. Yield: 0.9 g, mp 252°–253° C.

(B) Analogously to Example 1(D), 1.2 g of 17α-acetoxy-6α,16β-dimethyl-1,4,9(11)-pregnatriene-3,20-dione is reacted with N-bromosuccinimide and perchloric acid, worked up and purified, thus obtaining 1.3 g of 17α-acetoxy-9α-bromo-11β-hydroxy-6α,16β-dimethyl-1,4-pregnadiene-3,20-dione; this product is recrystallized from acetone/hexane; mp 184°–185° C.

(C) 300 mg of 17α-acetoxy-9α-bromo-11β-hydroxy-6α,16β-dimethyl-1,4-pregnadiene-3,20-dione is debrominated as described in Example 1(E) with tributyltin hydride, worked up, and purified, thus isolating 115 mg of 17α-acetoxy-11β-hydroxy-6α,16β-dimethyl-1,4-pregnadiene-3,20-dione, mp 270°–272° C.

EXAMPLE 7

(A) Under the conditions of Example 6(A), 3.0 g of 6α,16β-dimethyl-17α-propionyloxy-4,9(11)-pregnadiene-3,20-dione is dehydrogenated with dichlorodicyanobenzoquinone, worked up and purified, thus isolating 2.1 g of 6α,16β-dimethyl-17α-propionyloxy-1,4,9(11)-pregnatriene-3,20-dione, mp 220°–221° C.

(B) Analogously to Example 1(D), 2.0 g of 6α,16β-dimethyl-17α-propionyloxy-1,4,9(11)-pregnatriene-3,20-dione is reacted with N-bromosuccinimide and perchloric acid, worked up and purified, thus obtaining 2.1 g of 9α-bromo-11β-hydroxy-6α,16β-dimethyl-17α-propionyloxy-1,4-pregnadiene-3,20-dione, mp 175°–176° C.

(C) 500 mg of 9α-bromo-11β-hydroxy-6α,16β-dimethyl-17α-propionyloxy-1,4-pregnadiene-3,20-dione is debrominated analogously to Example 1(E) with tributyltin hydride, worked up and chromatographed. Yield: 270 mg of 11β-hydroxy-6α,16β-dimethyl-17α-propionyloxy-1,4-pregnadiene-3,20-dione, mp 260°–261° C.

EXAMPLE 8

(A) Analogously to Example 6(A), 4.75 g of 17α-butyryloxy-6α,16β-dimethyl-4,9(11)-pregnadiene-3,20-dione is reacted with dichlorodicyanobenzoquinone, worked up and purified, thus isolating 3.3 g of 17α-butyryloxy-6α,16β-dimethyl-1,4,9(11)-pregnatriene-3,20-dione, mp 195°–196° C.

(B) As described in Example 1(D), 3.2 g of 17α-butyryloxy-6α,16β-dimethyl-1,4,9(11)-pregnatriene-3,20-dione is reacted with N-bromosuccinimide and perchloric acid and worked up. Recrystallization from acetone/hexane yields 2.8 g of 9α-bromo-17α-butyryloxy-11β-hydroxy-6α,16β-dimethyl-1,4-pregnadiene-3,20-dione, mp 170°–171° C.

(C) 500 mg of 9α-bromo-17α-butyryloxy-11β-hydroxy-6α,16β-dimethyl-1,4-pregnadiene-3,20-dione is debrominated analogously to Example 1(E) with tributyltin hydride, worked up and chromatographed, thus isolating 350 mg of 17α-butyryloxy-11β-hydroxy-6α,16β-dimethyl-1,4-pregnadiene-3,20-dione, mp 190°–191° C.

EXAMPLE 9

A solution of 700 mg of 9α-bromo-17α-butyryloxy-11β-hydroxy-6α,16β-dimethyl-1,4-pregnadiene-3,20-dione in 1,4 ml of N-methylpyrrolidone is agitated with 700 mg of lithium chloride for 1.5 hours at a bath temperature of 80° C. After precipitation into ice water-sodium chloride, the mixture is worked up as usual, and the crude product is purified on 100 g of silica gel with a hexane-ethyl acetate gradient (0–50% ethyl acetate). Yield: 345 mg of 17α-butyryloxy-11β-hydroxy-6α,16β-dimethyl-1,4,8(9)-pregnatriene-3,20-dione, mp 222°–223° C.

EXAMPLE 10

(A) A suspension of 800 mg of 17α-acetoxy-9α-bromo-11β-hydroxy-6α,16β-dimethyl-1,4-pregnadiene-3,20-dione in 8 ml of acetone is stirred with 1.2 g of finely triturated potassium carbonate for 22 hours at room temperature. The potassium carbonate is suctioned off and the filtrate concentrated to dryness under vacuum. The crude product is purified on 100 g of silica gel with a hexane-ethyl acetate gradient (0–50% ethyl acetate), thus isolating 480 mg of 17α-acetoxy-9,11β-epoxy-6α,16β-dimethyl-1,4-pregnadiene-3,20-dione, mp 248°–250° C.

(B) A solution of 450 mg of 17α-acetoxy-9,11β-epoxy-6α,16β-dimethyl-1,4-pregnadiene-3,20-dione in 45 ml of chloroform is stirred with 9 ml of a 0.5N hydrochloric acid solution for 2.5 hours at room temperature. The mixture is diluted with methylene chloride, washed with a bicarbonate solution and then with water. The crude product is purified on 100 g of silica gel with a methylene chloride-acetone gradient (0–12% acetone). Yield: 260 mg of 17α-acetoxy-9α-chloro-11β-hydroxy-6α,16β-dimethyl-14-pregnadiene-3,20-dione, mp 268°–270° C.

EXAMPLE 11

(A) Analogously to Example 10(A), 1.5 g of 9α-bromo-11β-hydroxy-6α,16β-dimethyl-17α-propionyloxy-1,4-pregnadiene-3,20-dione is reacted with potassium carbonate, worked up and purified, thus isolating 1.2 g of 9,11β-epoxy-6α,16β-dimethyl-17α-propionyloxy-1,4-pregnadiene-3,20-dione, mp 212°–213° C.

(B) Under the conditions of Example 10(B), 500 mg of 9,11β-epoxy-6α,16β-dimethyl-17α-propionyloxy-1,4-pregnadiene-3,20-dione is reacted with 10 ml of 0.5N hydrochloric acid, worked up and purified, yielding 300 mg of 9α-chloro-11β-hydroxy-6α,16β-dimethyl-17α-propionyloxy-1,4-pregnadiene-3,20-dione, mp 248°–249° C.

EXAMPLE 12

(A) As described in Example 10(A), 2.5 g of 9α-bromo-17α-butyryloxy-11β-hydroxy-6α,16β-dimethyl-1,4-pregnadiene-3,20-dione is reacted with potassium carbonate, worked up and purified, thus obtaining 1.4 g of 17α-butyryloxy-9,11β-epoxy-6α,16β-dimethyl-1,4-pregnadiene-3,20-dione, mp 158°–160° C.

(B) Analogously to Example 10(B), 0.65 g of 17α-butyryloxy-9,11β-epoxy-6α,16β-dimethyl-1,4-pregnadiene-3,20-dione is reacted with 0.5N hydrochloric acid, worked up and purified, thus obtaining 0.6 g of 17α-butyryloxy-9α-chloro-11β-hydroxy-6α,16β-dimethyl-1,4-pregnadiene-3,20-dione, mp 224°–225° C.

EXAMPLE 13

300 mg of 17α-acetoxy-9,11β-epoxy-6α,16β-dimethyl-1,4-pregnadiene-3,20-dione is introduced into 1.2 ml of a solution of (HF)$_n$/pyridine, cooled to −40° C., and the solution is agitated for 4 hours between −40° C. and −10° C. After ammoniacal ice water precipitation, the precipitate is filtered off and worked up as usual. The crude product is purified on 100 g of silica gel with a methylene chloride-acetone gradient (0–12% acetone), thus producing 175 mg of 17α-acetoxy-9α-fluoro-11β-hydroxy-6α,16β-dimethyl-1,4-pregnadiene-3,20-dione, mp 291°–293° C.

EXAMPLE 14

As described in Example 13, 600 mg of 9,11β-epoxy-6α,16β-dimethyl-17α-propionyloxy-1,4-pregnadiene-3,20-dione is reacted with (HF)$_n$/pyridine, worked up and purified, yielding 410 mg of 9α-fluoro-11β-hydroxy-6α,16β-dimethyl-17α-propionyloxy-1,4-pregnadiene-3,20-dione, mp 269°–270° C.

EXAMPLE 15

Analogously to Example 13, 650 mg of 17α-butyryloxy-9,11β-epoxy-6α,16β-dimethyl-1,4-pregnadiene-3,20-dione is reacted with (HF)$_n$/pyridine, worked up and purified, thus isolating 570 mg of 17α-butyryloxy-9α-fluoro-11β-hydroxy-6α,16β-dimethyl-1,4-pregnadiene-3,20-dione, mp 246°–247° C.

EXAMPLE 16

(A) A solution of 30.0 g of 21-acetoxy-17α-hydroxy-6α,16β-dimethyl-4,9(11)-pregnadiene-3,20-dione in 800 ml of dioxane is reacted with 30.0 g of dichlorodicyanobenzoquinone analogously to Example 6(A), worked up and purified, yielding 12.0 g of 21-acetoxy-17α-hydroxy-6α,16β-dimethyl-1,4,9(11)-pregnatriene-3,20-dione, mp 215°–216° C.

(B) A solution is prepared from 10.5 g of 21-acetoxy-17α-hydroxy-6α,16β-dimethyl-1,4,9(11)-pregnatriene-3,20-dione in 7.5 ml of anhydrous methylene chloride and 50 ml of formaldehyde dimethylacetal and combined in incremental portions with a mixture of 15.0 g of kieselguhr W20 and 7.5 g of phosphorus pentoxide. The mixture is stirred for 1 hour at room temperature, suctioned off, and the residue is repeatedly eluted with methylene chloride containing 3–5% triethylamine. The crude product is purified on 1.5 kg of silica gel with a methylene chloride-acetone gradient (0–10% acetone), thus isolating 8.6 g of 21-acetoxy-17α-methoxymethoxy-6α,16β-dimethyl-1,4,9-pregnatriene-3,20-dione.

(C) A solution of 7.0 g of 21-acetoxy-17α-methoxymethoxy-6α,16β-dimethyl-1,4,9-pregnatriene-3,20-dione in 80 ml of methanolic 0.2N potassium hydroxide solution is stirred at 0° C. for 40 minutes, then neutralized with 10% acetic acid, yielding, after precipitation into ice water and working up of the reaction mixture, a crude product which is purified on 500 g of silica gel with a methylene chlorideacetone gradient (0–10% acetone). Yield: 4.3 g of 21-hydroxy-17α-methoxymethoxy-6α,16β-dimethyl-1,4,9-pregnatriene-3,20-dione.

(D) A solution of 4.0 g of 21-hydroxy-17α-methoxymethoxy-6α,16β-dimethyl-1,4,9-pregnatriene-3,20-dione in 40 ml of pyridine is combined at 0° C. dropwise with 2.1 ml of methanesulfonic acid chloride. The mixture is stirred for one hour at room temperature, and after ice water precipitation is worked up as usual. The crude product is purified on 300 g of silica gel with a methylene chloride-acetone gradient (0–10% acetone), thus isolating 2.9 g of 21-mesyloxy-17α-methoxymethoxy-6α,16β-dimethyl-1,4,9-pregnatriene-3,20-dione.

(E) A suspension of 980 mg of Cu(I) iodide in 20 ml of anhydrous tetrahydrofuran is cooled to −25° C. and combined with 11 ml of a 1.6-molar methyllithium solution. The mixture is stirred for about 0.5 hour at −25° C., cooled to −55° C., and a solution of 2.0 g of 21-mesyloxy-17α-methoxymethoxy-6α,16β-dimethyl-1,4,9-pregnatriene-3,20-dione in 20 ml of dimethylformamide is added dropwise thereto. After a reaction time of 2 hours at −55° C. to −5° C., a solution of 6.0 g of ammonium chloride in 30 ml of water is added gradually dropwise thereto, the mixture is further agitated at −5° C. for 15 minutes, diluted with ethyl acetate, and, after washing until neutral, worked up as usual. The crude product is purified on 200 g of silica gel with a methylene chloride-acetone gradient (0–10% acetone). In this way, 1.1 g of 17α-methoxymethoxy-6α,16β,21-trimethyl-1,4,9(11)-pregnatriene-3,20-dione is isolated.

(F) Analogously to Example 1(D), 1.0 g of 17α-methoxymethoxy-6α,16β,21-trimethyl-1,4,9(11)-pregnatriene-3,20-dione is reacted with N-bromosuccinimide and perchloric acid, worked up and purified, yielding 720 mg of 9α-bromo-11β-hydroxy-17α-methoxymethoxy-6α,16β,21-trimethyl-1,4-pregnadiene-3,20-dione.

(G) Under the conditions of Example 1(E), 700 mg of 9α-bromo-11β-hydroxy-17α-methoxymethoxy-6α,16β,21-trimethyl-1,4-pregnadiene-3,20-dione is debrominated with tributyltin hydride, worked up and purified, thus isolating 360 mg of 11β-hydroxy-17α-methoxymethoxy-6α,16β,21-trimethyl-1,4-pregnadiene-3,20-dione.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6α,16β-dimethyl corticoid of the formula

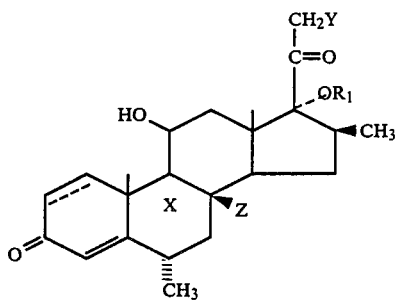

wherein
the bond ≡≡≡≡ represents a single or a double bond
Z jointly with X, is carbon-carbon bond, $R_1$ is formyl, alkanoyl or alkoxyalkyl each of 2–8 carbon atoms, or benzoyl, and
Y is hydrogen or methyl.

2. 17α-Butyryloxy-11β-hydroxy-6α,16β-dimethyl-1,4,8-(9) pregnatriene-3,20-dione, a compound of claim 1.

3. A pharmaceutical composition comprising a pharmaceutically effective amount of a compound of claim 1 and a pharmacologically acceptable carrier.

4. A composition of claim 3 adapted for topical administration.

5. A method of topically treating an inflammation in a patient comprising administering an amount of a compound of claim 1 effective for such treatment.

6. A compound of claim 1 wherein $R_1$ is alkoxyalkyl.

7. A compound of claim 1, wherein Y is methyl.

* * * * *